United States Patent
Becker et al.

(10) Patent No.: US 9,175,148 B2
(45) Date of Patent: Nov. 3, 2015

(54) $C_{11}$ TO $C_{13}$ DIALKYL ESTERS OF FURANDICARBOXYLIC ACID AS SOFTENERS

(75) Inventors: Hinnerk Gordon Becker, Essen (DE); Michael Grass, Haltern am See (DE)

(73) Assignee: EVONIK DEGUSSA GmbH, Essen (DE)

( * ) Notice: Subject to any disclaimer, the term of this patent is extended or adjusted under 35 U.S.C. 154(b) by 138 days.

(21) Appl. No.: 14/001,338

(22) PCT Filed: Jan. 27, 2012

(86) PCT No.: PCT/EP2012/051304
§ 371 (c)(1),
(2), (4) Date: Sep. 5, 2013

(87) PCT Pub. No.: WO2012/113607
PCT Pub. Date: Aug. 30, 2012

(65) Prior Publication Data
US 2013/0338276 A1  Dec. 19, 2013

(30) Foreign Application Priority Data
Feb. 24, 2011 (DE) .......................... 10 2011 004 675

(51) Int. Cl.
C08K 5/1535 (2006.01)
C07D 307/68 (2006.01)
C08K 5/00 (2006.01)

(52) U.S. Cl.
CPC ............ *C08K 5/1535* (2013.01); *C07D 307/68* (2013.01); *C08K 5/0016* (2013.01); *C08K 2201/014* (2013.01)

(58) Field of Classification Search
CPC ............. C08K 5/1535; C08K 15/0016; C08K 2201/014; C07D 307/68
See application file for complete search history.

(56) References Cited

U.S. PATENT DOCUMENTS

2012/0202725 A1  8/2012  Grass et al.
2012/0220507 A1  8/2012  Grass et al.

FOREIGN PATENT DOCUMENTS

| WO | WO 2011/023590 A1 | 3/2011 |
| WO | WO 2011/061123 A1 | 5/2011 |
| WO | WO 2012/113607 A1 | 8/2012 |
| WO | WO 2012/113608 A1 | 8/2012 |
| WO | WO 2012/113609 A1 | 8/2012 |

OTHER PUBLICATIONS

R. D. Sanderson et al., "Synthesis and Evaluation of Dialkyl Furan-2,5-Dicarboxylates as Plasticizers for PVC", Journal of Applied Polymer Science, vol. 53, No. 13, XP-000464476, Sep. 26, 1994, pp. 1785-1793.

*Primary Examiner* — Kriellion Sanders
(74) *Attorney, Agent, or Firm* — Oblon, McClelland, Maier & Neustadt, L.L.P.

(57) ABSTRACT

The invention relates to $C_{11}$ to $C_{13}$ dialkyl esters of furandicarboxylic acid.

23 Claims, No Drawings

$C_{11}$ TO $C_{13}$ DIALKYL ESTERS OF FURANDICARBOXYLIC ACID AS SOFTENERS

CROSS REFERENCE TO RELATED APPLICATIONS

The present application is a 35 U.S.C. §371 national stage patent application of International patent application PCT/EP201/051304, filed on Jan. 27, 2012, published as WO/2012/113607 on Aug. 30, 2012, the text of which is incorporated by reference, and claims the benefit of the filing date of German application no. 102011004675.5, filed on Feb. 24, 2011, the text of which is also incorporated by reference.

The present invention relates to $C_{11}$ to $C_{13}$ dialkyl esters of furandicarboxylic acid and mixtures thereof.

The invention further relates to plasticizers comprising $C_{11}$ to $C_{13}$ dialkyl esters of furan dicarboxylic acid and mixtures thereof. The invention further provides for the use of these plasticizers in polymers, especially PVC, and a process for producing the plasticizer. The invention further provides mouldings or films formed from these polymers, and for the use of the plasticizers for various applications.

Polyvinyl chloride (PVC) is one of the most economically important polymers and is used in various applications both in the form of rigid PVC and in the form of flexible PVC. Important areas of use are, for example, cable sheathing, floor coverings, wallpaper and frames for plastic windows. To increase the elasticity and for better processability, plasticizers are added to the PVC. These customary plasticizers include, for example, phthalic esters such as di-2-ethylhexyl phthalate (DEHP), diisononyl phthalate (DINP) and diisodecyl phthalate (DIDP). Due to their toxicological properties, there are efforts in many cases to replace phthalic esters with other plasticizers. Alternative plasticizers which have been described recently are therefore, for example, cyclohexanedicarboxylic esters such as diisononyl cyclohexanedicarboxylate (DINCH).

In addition, the prior art has also described esters of terephthalic acid, especially di-2-ethylhexyl terephthalate (DENT or DOTP), as alternative plasticizers.

WO 2009/095126 A1 describes mixtures of diisononyl esters of terephthalic acid, and processes for preparation thereof. These plasticizers have an average degree of branching of the isononyl radicals which is in the range from 1.0 to 2.2, and are likewise used as plasticizers for PVC.

Due to the limited availability of fossil raw materials, the associated significant price rises which are foreseeable in the future, and the use of renewable raw materials, for which there is also ever greater political demands, particularly those esters in which at least the acid component is based on naturally occurring resources, such as sugars, fats or oils, should have good market opportunities in the future.

Many esters of furandicarboxylic acid, for example di-n-butyl furan-2,5-dicarboxylate and di-n-hexyl furan-2,5-dicarboxylate, are crystalline solids at room temperature and, due to their solid nature, cannot be used for the production of plastisols. Thus, the production of polymer pastes or plastisols on the industrial scale can be achieved only with liquid plasticizers. Solid plasticizers have to be dissolved beforehand in appropriate solvents, which makes the process inconvenient and costly.

Furandicarboxylates with higher monohydric alcohols than C8 are as yet unknown, and therefore also have not as yet been described as plasticizers for polymers. For applications in which high demands are made on the emissions characteristics, for example high-temperature cables or automobile interior trim, there are therefore barely any suitable plasticizers based on renewable raw materials.

To date, the esters of phthalic acid have also been used for these applications, but they are classified as critical due to their toxicological properties and, furthermore, cannot be produced from renewable raw materials.

Proceeding from this prior art, the technical object of the invention is to provide novel substances which can be produced in a simple manner from renewable raw materials and have good plasticizer properties compared to the plasticizers used to date.

The technical problem addressed by the invention is solved by $C_{11}$ to $C_{13}$ dialkyl esters of furandicarboxylic acid.

It has been found that, surprisingly, $C_{11}$-$C_{13}$ dialkyl esters of furandicarboxylic acid can be used as plasticizers or as a constituent of a plasticizer composition for polymers, especially for polyvinyl chloride (PVC), polyvinyl butyral (PVB) and polyalkyl methacrylate (PAMA), and have advantageous properties therein, compared to the analogous phthalic esters typically used as plasticizers.

The inventive plasticizers have shorter dry blend times compared to the analogous prior art phthalate plasticizers. This means that a shorter mixing time is needed in the production of dry blends (=pulverulent mixtures of polymer, especially PVC, and further formulation constituents; the liquid formulation constituents are absorbed by the polymer particles in the mixing operation), and this gives rise to a cost advantage over the prior art plasticizers. A further advantage of the inventive plasticizers lies in the low volatility. This is lower than in the case of the corresponding phthalate plasticizers, and so the loss of plasticizer as a result of sweating or vaporization is less severe, and therefore reliable processing of the plasticizer in the polymer is possible. It has additionally been found that the inventive plasticizers have better plasticizing action and hence a higher efficiency when compared to the corresponding prior art phthalate plasticizers.

In a preferred embodiment, the plasticizer comprises a $C_{11}$-$C_{13}$ dialkyl furan-2,5-dicarboxylate.

It is additionally preferred that the plasticizer comprises at least two isomeric $C_{11}$-$C_{13}$ dialkyl furan-2,5-dicarboxylates. These isomeric $C_{11}$-$C_{13}$ dialkyl furan-2,5-dicarboxylates contain isomeric $C_{11}$-$C_{13}$ alkyl groups. In a particularly preferred manner, these are isomeric $C_{11}$-$C_{13}$ alkyl groups selected from the group of unbranched alkyl group, singly branched alkyl group, doubly branched alkyl group, triply branched alkyl group, quadruply branched alkyl group and mixtures thereof.

In a preferred embodiment, none of the isomeric $C_{11}$-$C_{13}$ dialkyl furan-2,5-dicarboxylates is present in the ester mixture in a proportion of more than 90% by weight. It is additionally preferred that the proportion of unbranched $C_{11}$-$C_{13}$ alkyl groups in the ester mixture is within a range from 0.01 to 80% by weight.

In a very particularly preferred embodiment, the plasticizer is characterized in that it comprises ditridecyl furan-2,5-dicarboxylate. Because of their particularly low volatility, these products are very particularly suitable for production of products with high demands on long lifetime due to low vaporization tendency.

In a further preferred embodiment, the plasticizer may comprise additional other plasticizers, which are especially selected from the group of alkyl benzoates, dialkyl adipates, glyceryl esters, epoxidized vegetable oils; saturated or unsaturated fatty acid esters which may also be partially or fully epoxidized; trialkyl citrates, acylated trialkyl citrates, trialkyl mellitates, glycol dibenzoates, dialkyl terephthalates, dialkyl phthalates, isosorbide esters, especially dialkanoyl esters of isosorbitol, dialkyl esters of 1,2-, 1,3- or 1,4-cyclohexanedicarboxylic acid. These additional plasticizers are specifically selected, for example, from the following list:

Dialkyl phthalates, preferably having 4 to 13 carbon atoms in the alkyl chain; trialkyl trimellitates, preferably having 4 to 10 carbon atoms in the side chain; dialkyl adipates, preferably having 4 to 13 carbon atoms; dialkyl terephthalates, preferably each having 4 to 10 carbon atoms, especially 7 to 9 carbon atoms, in the side chain; alkyl 1,2-cyclohexanedicarboxylates, alkyl 1,3-cyclohexanedicarboxylates and alkyl 1,4-cyclohexanedicarboxylates, preference being given here to alkyl 1,2-cyclohexanedicarboxylates, preferably in each case with 4 to 13 carbon atoms in the side chain; dibenzoic esters of glycols; alkylsulphonic esters of phenol with preferably one alkyl radical containing 8 to 22 carbon atoms; glyceryl esters; citric triesters with a free or carboxylated OH group and, for example, alkyl radicals of 4 to 10 carbon atoms, alkylpyrrolidone derivatives with alkyl radicals of 4 to 18 carbon atoms and alkyl benzoates, preferably with 8 to 13 carbon atoms in the alkyl chain. In all cases, the alkyl radicals may be linear or branched and identical or different.

More preferably, in the inventive mixtures, no ortho-phthalate is used as additional plasticizer.

In a particular embodiment, at least one of the additional plasticizers used in the inventive composition is a trialkyl trimellitate. This trialkyl trimellitate preferably has ester side chains having 4 to 10 carbon atoms, where the ester groups may have either the same or a different number of carbon atoms. More preferably, at least one of the ester groups present is a group having not less than 8 carbon atoms per ester group, especially preferably a group having not less than 9 carbon atoms and most preferably a group having not less than 10 carbon atoms.

In a further particular embodiment, at least one of the additional plasticizers used in the inventive composition is a dialkyl adipate. This dialkyl adipate preferably has ester side chains having 4 to 13 carbon atoms, where the ester groups here too may have either the same or a different number of carbon atoms. More preferably, at least one of the ester groups present is a group having not less than 8 carbon atoms per ester group, especially preferably a group having not less than 10 carbon atoms and most preferably a group having 13 carbon atoms.

More particularly, at least one of the dialkyl adipates used is diethylhexyl adipate, diisononyl adipate, diisodecyl adipate, dipropylheptyl adipate or diisotridecyl adipate.

In a further particular embodiment, at least one of the additional plasticizers used in the inventive composition is a dialkyl terephthalate. This dialkyl terephthalate preferably has ester side chains having 4 to 10 carbon atoms, where the ester groups may again have either the same or a different number of carbon atoms. More preferably, at least one of the ester groups present is a group having not less than 4 carbon atoms per ester group, especially preferably a group having not less than 9 carbon atoms and most preferably a group having 10 carbon atoms. More particularly, at least one of the dialkyl terephthalates used is di-n-heptyl terephthalate, di-iso-heptyl terephthalate, di-n-butyl terephthalate, di(3-methylbutyl) terephthalate, di-n-pentyl terephthalate, di-2-ethylhexyl terephthalate or diisononyl terephthalate.

In a further particular embodiment, at least one of the additional plasticizers used in the inventive composition is a dialkyl ester of cyclohexanedicarboxylic acid, more preferably a dialkyl ester of 1,2-cyclohexanedicarboxylic acid. Preferably, this dialkyl cyclohexanedicarboxylate has ester side chains having 4 to 13 carbon atoms, where the ester groups may again either have the same or a different number of carbon atoms. More preferably, at least one of the ester groups present is a group having not less than 5 carbon atoms per ester group, especially preferably a group having not less than 9 carbon atoms and most preferably a group having not less than 10 carbon atoms. More particularly, at least one of the dialkyl cyclohexanedicarboxylates used is di-n-pentyl 1,2-cyclohexanedicarboxylate, di-n-heptyl 1,2-cyclohexanedicarboxylate, di-iso-heptyl 1,2-cyclohexanedicarboxylate or di-(3-methylbutyl) 1,2-cyclohexanedicarboxylate, di-2-ethylhexyl 1,2-cyclohexanedicarboxylate, di-2-ethylhexyl 1,3-cyclohexanedicarboxylate, di-2-ethylhexyl 1,4-cyclohexanedicarboxylate, and also diisononyl 1,2-cyclohexanedicarboxylate, diisononyl 1,3-cyclohexanedicarboxylate and diisononyl 1,4-cyclohexanedicarboxylate.

In a further particular embodiment, at least one of the additional plasticizers used in the inventive composition is a glyceryl ester, more preferably a glyceryl triester. The ester groups may either be of aliphatic or aromatic structure. This glyceryl ester preferably has ester side chains having 1 to 9 carbon atoms, where the ester groups may again have either the same or a different number of carbon atoms, and may be linear or branched, saturated or unsaturated, or else may contain one or more epoxide units. More preferably, at least one of the ester groups present is a group having not less than 2 carbon atoms per ester group, especially preferably a group having not less than 8 carbon atoms and most preferably a group having 9 carbon atoms. It is additionally possible with preference to use glyceryl esters with ester side chains having 1 to 24 carbon atoms, where the ester groups may again have either the same or a different number of carbon atoms. More preferably, one of the ester groups is hydroxystearic acid, where the hydroxyl function is preferably likewise esterified, more preferably by an acetyl group. Additionally preferably, at least one of the ester groups is lauric acid.

In a further particular embodiment, at least one of the additional plasticizers used in the inventive composition is a citric triester with a free or carboxylated OH group. The ester groups here too may be either of aliphatic or aromatic structure. The citric triester is especially preferably a trialkyl citrate with a carboxylated OH group. This trialkyl citrate preferably has ester side chains having 2 to 10 carbon atoms, where the ester groups may again have either the same or a different number of carbon atoms. More preferably, at least one of the ester groups present is a group having not less than 4 carbon atoms per ester group, especially preferably a group having not less than 8 carbon atoms and most preferably a group having not less than 9 carbon atoms. More particularly, at least one of the citric esters used is acetyl tributyl citrate, acetyl tri-n-butyl citrate, acetyl tri-n-pentyl citrate, acetyl tri-iso-heptyl citrate, acetyl tri-2-ethylhexyl citrate or acetyl tri-isononyl citrate.

In a preferred embodiment, the mass ratio of additional plasticizers used and the $C_{11}$ to $C_{13}$ dialkyl esters of furandicarboxylic acid is between 1:20 and 20:1, more preferably from 1:20 to 10:1 and most preferably from 1:20 to 5:1.

In addition to the plasticizer itself, a process for production thereof is also claimed. Such a process comprises the process steps of:
  a) reacting a stoichiometric excess of $C_{11}$-$C_{13}$-alcohols, optionally in the presence of a catalyst, with furandicarboxylic acid or a correspondingly suitable derivative of furandicarboxylic acid
  b) removing the excess alcohol after complete conversion of the furandicarboxylic acid or of the correspondingly suitable derivative to the $C_{11}$-$C_{13}$-dialkyl ester of furandicarboxylic acid and c) working up the reaction mixture to obtain the inventive product in high purity.

An alternative process for preparing a $C_{11}$ to $C_{13}$ dialkyl ester of the furandicarboxylic acid comprises the following process steps:

a) contacting 5-hydroxymethylfurfural and/or at least one furan derivative with one or more aliphatic alcohols having 11-13 carbon atoms, and at least one catalyst and at least one oxygen-containing component, b) adjusting the temperature of the reaction mixture described to >0° C. and performing an oxidative esterification, the term "oxidative esterification" being understood to mean (any) combination of oxidation and esterification and, if appropriate, the detachment of a protecting group from the furan derivative in preferably one process step, especially preferably in one reaction space.

The inventive $C_{11}$ to $C_{13}$ dialkyl esters of furandicarboxylic acid can be prepared by esterification of the furandicarboxylic acid or by transesterification, for example from the methyl esters of furandicarboxylic acid.

The process according to the invention for preparing isomeric $C_{11}$-$C_{13}$-dialkyl esters of 2,5-furandicarboxylic acid is notable in that 2,5-furandicarboxylic acid or a relatively short-chain dialkyl ester of this compound, preferably the dimethyl ester, is reacted with a mixture of isomeric $C_{11}$-$C_{13}$-alcohols with optional use of a catalyst. In addition, the starting material used to prepare the furandicarboxylic esters may also be 2,5-furandicarbonyl dichloride, which can be obtained by reaction of FDCA with chlorinating agents, for example thionyl chloride. Preference is given to using a mixture of isomeric $C_{11}$-$C_{13}$-alcohols, especially a mixture of isomeric $C_{12}$-$C_{13}$-alcohols and most preferably a mixture of isomeric $C_{13}$-alcohols.

Preparation of the Isomeric Alcohol Mixtures

Processes for preparing the corresponding alcohol mixtures are known from the literature. The most important process for preparation is the hydroformylation of corresponding olefins or olefin mixtures having one fewer carbon atom compared to the alcohol with subsequent hydrogenation to give the corresponding alcohol mixtures. In the case of preparation of tridecyl alcohol, the preparation is effected, for example, from tributene or tetrapropylene ($C_{12}$-olefin). Hydroformylation processes are described in DE 199 55 593 A1 and EP 1515934 A1.

The olefins used for hydroformylation may all have the same carbon atom number, for example the $C_{12}$-olefins obtainable as a by-product from the Octol process, which are also known by the tributene name. A mixture of isomeric $C_{13}$-alcohols known on the market is Marlipal O13 sold by Sasol, or Isotridecanol N from BASF.

In addition, these olefins may also originate from distillation cuts which comprise olefins with different carbon atom numbers, as known, for example, from the Polygas process, and produced and converted to the alcohols, for example, by ExxonMobil Chemical (e.g. Exxal 13). The phthalate plasticizer obtainable therefrom has been known on the market for many years as JAYFLEX DTDP.

In addition to the alcohols preparable by hydroformylation, there are also further known processes. Examples here include the Alfol process for preparation of even-numbered linear alcohols, but also the hydrogenation of fatty acids or fatty acid esters, especially fatty acid methyl esters. An overview of processes for hydrogenation of the aldehydes to the corresponding alcohols can be found, for example, in EP 1749572 A1.

Esterification

To prepare the inventive esters, either 2,5-furandicarboxylic acid or a reactive derivative, for example the corresponding dichloride or the dimethyl ester, is reacted with a mixture of isomeric $C_{11}$-$C_{13}$-alcohols. The esterification preferably proceeds from furandicarboxylic acid or dimethyl furandicarboxylate, and more preferably from dimethyl furandicarboxylate and the appropriate $C_{11}$-$C_{13}$-alcohols, with the aid of a catalyst.

The esterification of the furandicarboxylic acid with a $C_{11}$-$C_{13}$ alcohol mixture to give the corresponding esters can be performed autocatalytically or catalytically, for example with Brønsted or Lewis acids. No matter what kind of catalysis is selected, the result is always a temperature-dependent equilibrium between the acid and alcohol feedstocks and the ester and water products. In order to shift the equilibrium in favour of the ester, it is possible to use an entraining agent, with the aid of which the water of reaction is removed from the mixture. Since the alcohol mixtures used for the esterification have a lower boiling point than the furandicarboxylic acid, the reactive derivatives thereof and esters thereof and have a miscibility gap with water, they are frequently used as an entraining agent which, after removal of water, can be recycled back into the process.

The alcohol used to form the ester or the isomeric $C_{11}$-$C_{13}$ mixture which serves simultaneously as an entraining agent is used in excess, preferably in an excess of 5 to 120% by mass, especially of 10 to 80% by mass, of the amount needed to form the ester.

The esterification catalysts used may be acids, for example sulphuric acid, methanesulphonic acid or p-toluenesulphonic acid, or metals or compounds thereof. Suitable examples are tin, titanium, zirconium, which are used in the form of finely divided metals or appropriately in the form of salts thereof, oxides or soluble organic compounds. In contrast to protic acids, the metal catalysts are high-temperature catalysts which often attain their full activity only at temperatures above 180° C. However, it should be noted in this context that the furandicarboxylic acid tends to eliminate $CO_2$ at temperatures above 190° C. to form the monocarboxylic acid, which of course then can no longer be converted to the target product. In the case of use of dimethyl furandicarboxylate, these disadvantages do not exist.

However, the metal catalysts are used with preference because, compared to protic catalysis, they form a lower level of by-products, for example olefins from the alcohol used. Illustrative representatives of metal catalysts are tin powder, tin(II) oxide, tin(II) oxalate, titanic esters such as tetraisopropyl orthotitanate or tetrabutyl orthotitanate, and zirconium esters such as tetrabutyl zirconate.

The catalyst concentration depends on the type of catalyst. In the case of the titanium compounds used with preference, the concentration is 0.005 to 2.0% by mass based on the reaction mixture, especially 0.01 to 0.5% by mass, very preferably 0.01 to 0.1% by mass.

The reaction temperatures in the case of use of titanium catalysts are between 160° C. and 270° C., preferably 160° C. to 200° C. The optimal temperatures depend on the feedstocks, reaction progress and catalyst concentration. They can be determined easily by tests for each individual case. Higher temperatures increase the reaction rates and promote side reactions, for example elimination of water from alcohols or formation of coloured by-products. It is favourable for removal of the water of reaction that the alcohol can be distilled out of the reaction mixture. The desired temperature or the desired temperature range can be established by the pressure in the reaction vessel. In the case of low-boiling alcohols the reaction is therefore performed at elevated pressure, and in the case of higher-boiling alcohols under reduced pressure. For example, the reaction of FDCA with a mixture of isomeric tridecanols is conducted within a temperature range of 160° C. to 190° C. within the pressure range from 0.1 MPa to 0.001 MPa.

The amount of liquid to be recycled into the reaction may consist partly or entirely of alcohol which is obtained by workup of the azeotropic distillate. It is also possible to conduct the workup at a later time and to replace the amount of liquid removed completely or partially with fresh alcohol, i.e. alcohol available in a reservoir vessel.

The crude ester mixtures which comprise, in addition to the ester(s), alcohol, catalyst or conversion products thereof and possibly by-products, are worked up by processes known per se. The workup comprises the following steps: removal of the excess alcohol and any low boilers, neutralization of the acids present, optionally a steam distillation or stripping with inert gas, conversion of the catalyst to a readily filterable residue, removal of the solids and optionally drying. According to the workup process employed, the sequence of these steps may be different.

Optionally, the mixture of the $C_{11}$ to $C_{13}$ dialkyl esters of furandicarboxylic acid can be removed by distillation from the reaction mixture, optionally after neutralization of the mixture.

Transesterification

Alternatively, the inventive $C_{11}$ to $C_{13}$ dialkyl esters of furandicarboxylic acid can be obtained by transesterifying a furan-2,5-dicarboxylic diester with a $C_{11}$ to $C_{13}$ alcohol mixture. The reactants used are furan-2,5-dicarboxylic diesters whose alkyl radicals bonded to the oxygen atom of the ester group have 1-10 carbon atoms. These radicals may be aliphatic, straight-chain or branched, and alicyclic or aromatic. One or more methylene groups of these alkyl radicals may be substituted by oxygen. It is appropriate that the parent alcohols of the reactant ester have a lower boiling point than the $C_{11}$ to $C_{13}$ alcohol mixture used. A preferred feedstock is dimethyl furan-2,5-dicarboxylate.

The transesterification is performed catalytically, for example with Brønsted or Lewis acids or bases. No matter which catalyst is used, the result is always a temperature-dependent equilibrium between the feedstocks, dialkyl esters of furandicarboxylic acid and $C_{11}$ to $C_{13}$ alcohol mixture, and the products, $C_{11}$ to $C_{13}$ dialkyl esters of furandicarboxylic acid and alcohol released. In order to shift the equilibrium in favour of the $C_{11}$ to $C_{13}$ dialkyl esters of the furandicarboxylic acid, the alcohol formed from the reactant ester is distilled out of the reaction mixture. It is also appropriate here to use the $C_{11}$ to $C_{13}$ alcohol mixture in excess.

The transesterification catalysts used may be acids, for example sulphuric acid, methanesulphonic acid or p-toluenesulphonic acid, or metals or compounds thereof. Suitable examples are tin, titanium, zirconium, which are used in the form of finely divided metals or appropriately in the form of salts thereof, oxides or soluble organic compounds. Unlike protic acids, the metal catalysts are high-temperature catalysts which attain their full activity only at temperatures above 180° C. However, they are used with preference because they form a lower level of by-products compared to protic catalysis, for example olefins from the alcohol used. Illustrative representatives of metal catalysts are tin powder, tin(II) oxide, tin(II) oxalate, titanic esters such as tetraisopropyl orthotitanate or tetrabutyl orthotitanate, tetraisotridecyl orthotitanate, and zirconium esters such as tetrabutyl zirconate or tetraisotridecyl zirconate.

In addition, it is possible to use basic catalysts, for example oxides, hydroxides, hydrogencarbonates, carbonates or alkoxides of alkali metals or alkaline earth metals. From this group, preference is given to using alkoxides, for example sodium methoxide. Alkoxides can also be prepared in situ from an alkali metal and a $C_{11}$ to $C_{13}$ alcohol.

The catalyst concentration depends on the type of catalyst. It is typically between 0.005 to 2.0% by mass based on the reaction mixture.

The reaction temperatures for the transesterification are typically between 100° C. and 250° C. They must be at least sufficiently high that the alcohol formed from the reactant ester can be distilled out of the reaction mixture at the given pressure, usually standard pressure.

The transesterification mixtures can be worked up in the same way as described for the esterification mixtures; it may be possible to dispense with a neutralization.

In addition to the inventive esters, the use thereof as or in plasticizer(s) for polymers, especially PVC, is also claimed.

Additionally claimed is the use of the above-described inventive esters in adhesives, sealing compounds, coating compositions, lacquers, paints, plastisols, synthetic leather, floor coverings, underbody protection, fabric coatings, cables or wire insulation, extruded articles, and in films, especially for the automobile interior sector, and also in wallpaper or inks.

Additionally claimed are polymers comprising at least one of the above-described plasticizers.

The inventive plasticizers can be used for modification of polymers. These polymers are preferably selected from the group consisting of:

polyvinyl chloride (PVC), polyvinylidene chloride (PVDC), polyacrylates, especially polymethyl methacrylate (PMMA), polyalkyl methacrylate (PAMA), fluoropolymers, especially polyvinylidene fluoride (PVDF), polytetrafluoroethylene (PTFE), polyvinyl acetate (PVAc), polyvinyl alcohol (PVA), polyvinyl acetals, especially polyvinyl butyral (PVB), polystyrene polymers, especially polystyrene (PS), expandable polystyrene (EPS), acrylonitrile-styrene-acrylate copolymers (ASA), styrene acrylonitrile copolymers (SAN), acrylonitrile-butadiene-styrene copolymers (ABS), styrene-maleic anhydride copolymers (SMA), styrene-methacrylic acid copolymers, polyolefins and/or polyolefin copolymers, especially polyethylene (PE) or polypropylene (PP), thermoplastic polyolefins (TPO), polyethylene-vinyl acetate copolymers (EVA), polycarbonates, polyethylene terephthalate (PET), polybutylene terephthalate (PBT), polyoxymethylene (POM), polyamide (PA), polyethylene glycol (PEG), polyurethane (PU), thermoplastic polyurethane (TPU), polysulphides (PSu), biopolymers, especially polylactic acid (PLA), polyhydroxybutyral (PHB), polyhydroxyvaleric acid (PHV), polyesters, starch, cellulose and cellulose derivatives, especially nitrocellulose (NC), ethylcellulose (EC), cellulose acetate (CA), cellulose acetate/butyrate (CAB), rubber or silicones, and mixtures or copolymers of the polymers mentioned or monomeric units thereof. The inventive polymers preferably comprise PVC or homo- or copolymers based on ethylene, propylene, butadiene, vinyl acetate, glycidyl acrylate, glycidyl methacrylate, methyl acrylates, ethyl acrylates, butyl acrylates or methacrylates with alkyl radicals, bonded to the oxygen atom of the ester group, of branched or unbranched alcohols having one to ten carbon atom(s), styrene, acrylonitrile or cyclic olefins.

The polymer is more preferably polyvinyl acetate, polyalkyl methacrylate or a copolymer of vinyl chloride with one or more monomers selected from the group consisting of vinylidene chloride, vinyl acetate, vinyl propionate, vinyl butyrate, vinyl benzoate, methyl acrylate, ethyl acrylate or butyl acrylate.

The polymer preferably comprises, as the PVC type, suspension, bulk, microsuspension or emulsion PVC.

Based on 100 parts by mass of polymer, the inventive polymers comprise preferably from 5 to 200, more preferably from 10 to 150, parts by mass of plasticizer. In particular cases, the ratio of plasticizer to polymer may be in the range from 1:15 to 15:1.

The inventive polymers may comprise, in addition to the constituents mentioned, additives which are especially selected from the group consisting of fillers, pigments, thermal stabilizers, costabilizers, UV stabilizers, antioxidants, viscosity regulators, flame retardants and lubricants.

The thermal stabilizers neutralize, inter alia, hydrochloric acid eliminated during and/or after the processing of the PVC and prevent thermal degradation of the polymer. Useful thermal stabilizers include all customary PVC stabilizers in solid and liquid form, for example based on Ca/Zn, Ba/Zn, Pb, Sn or organic compounds (OBS), and also acid-binding sheet silicates such as hydrotalcite. The inventive mixtures may have a content of 0.5 to 12, preferably 1 to 10 and more preferably 1.5 to 8 parts by mass of thermal stabilizer per 100 parts by mass of polymer. The so-called costabilizers (i.e. substances which prolong, improve and/or supplement the effect of the thermal stabilizers) used may, for example, be vegetable oil derivatives, for example epoxidized soybean oil or epoxidized linseed oil.

The pigments used in the context of the present invention may be either inorganic or organic pigments. The content of pigments is between 0.01 to 10% by mass, preferably 0.05 to 5% by mass and more preferably 0.1 to 3% by mass per 100 parts by mass of polymer. Examples of inorganic pigments are $TiO_2$, CdS, $CoO/Al_2O_3$, $Cr_2O_3$. Known organic pigments are, for example, azo dyes, phthalocyanine pigments, dioxazine pigments and aniline pigments.

The inventive polymers may comprise all fillers corresponding to the prior art. Examples of such fillers are mineral and/or synthetic and/or natural, organic and/or inorganic materials, for example calcium oxide, magnesium oxide, calcium carbonate, barium sulphate, silicon dioxide, sheet silicate, industrial carbon black, bitumen, wood (e.g. pulverized, as pellets, micropellets, fibres, etc.), paper, natural and/or synthetic fibres. More preferably, at least one of the fillers used is a calcium carbonate or a calcium magnesium carbonate.

The inventive esters are preferably in liquid form, especially in the form of a pumpable liquid.

The inventive plasticizers can be used in adhesives, sealing compounds, lacquers, paints, plastisols, synthetic leather, floor coverings, underbody protection, fabric coatings, cables, wallpaper or inks. Particular preference is given to use in high-temperature cables and automobile interior trim such as films for dashboards.

The invention further provides mouldings or films comprising the inventive polymers.

These mouldings or films are preferably a floor covering, a wall covering, a hose, a profile, a roofing sheet, a sealing sheet, a cable and wire sheath, a tarpaulin, an advertising banner, synthetic leather, packaging film, a medical article, a toy, a seal, a furnishing article. The moulding or the film is preferably a cable sheath for a high-temperature cable or a constituent of automobile interior trim, especially a film for the dashboard.

The examples which follow are intended to illustrate the invention without restricting the range of application thereof, which is evident from the description and the claims.

EXAMPLES

Example 1

Synthesis of diisotridecyl furan-2,5-dicarboxylate

A 4 liter stirred flask with water separator with attached jacketed coil condenser, stirrer, immersed tube, dropping funnel and thermometer was initially charged with 234 g (1.5 mol) of furan-2,5-dicarboxylic acid, 0.59 g (0.25% by mass based on furan-2,5-dicarboxylic acid) of tetrabutyl orthotitanate and 1200 g (6 mol) of isotridecanol prepared via the OCTOL process (Marlipal O13, from Sasol), which were esterified at 170° C. After 26 hours, the reaction had ended and then the excess alcohol was distilled off up to 210° C. and 3 mbar. This was followed by cooling to 80° C. and neutralization with 2 ml of a 10% by mass aqueous NaOH solution. Thereafter, purification was conducted at 200° C. and a pressure of 30 mbar by stripping with nitrogen. For this purpose, at maximum vacuum (1 mbar at a suction output of 5 $m^3$/h), the pressure was adjusted via the nitrogen flow rate. Thereafter, the mixture was cooled to 100° C. and then filtered. GC gave an ester content of >99.5%.

Example 2 (Comparative Example)

Synthesis of Diisotridecyl Phthalate

A 4 liter stirred flask with water separator with attached jacketed coil condenser, stirrer, immersed tube, dropping funnel and thermometer was initially charged with 592 g (4 mol) of phthalic anhydride (Fluka), 0.71 g (0.25% by mass based on phthalic anhydride) of tetrabutyl orthotitanate and 2000 g (10 mol) of isotridecanol prepared via the OCTOL process (Marlipal O13, from Sasol), which were esterified up to 240° C. After 3 hours, the reaction had ended, and then the excess alcohol was distilled off up to 210° C. and 3 mbar. This was followed by cooling to 80° C. and neutralization with 6 ml of a 10% by mass aqueous NaOH solution. Thereafter, a steam distillation (8% by mass of water based on the amount of ester) was conducted at 200° C. Thereafter, the mixture was cooled to 100° C. and then filtered. GC gave an ester content of >99.5%.

Example 3 (Comparative Example)

Synthesis of Diisotridecyl Terephthalate

Example 3 was performed like Example 2, except with the difference that 664 g (4 mol) of terephthalic acid (Merck) were used instead of phthalic anhydride. In accordance with the altered amount of acid, the amount of catalyst was also adjusted. GC gave an ester content of >99.5%.

Example 4

Determination of the Dissolution Temperature

The dissolution temperature is an important indication of the gelling capacity of a plasticizer.
Description of the Test:
96 g of the appropriate plasticizer of Examples 1 to 3 and 4 g of the PVC Lacovyl PB 1704 H (from Arkema) are weighed into a 150 ml beaker. A magnetic stirrer bar and an internal thermometer secured to a clamp stand (range: 0° C.-250° C., display accuracy: 0.5° C.) are added to the mixture. A wire or adhesive tape is used to secure a paper strip bearing the message "Lösetemperatur" in the font "Times New Roman", font size 12, to the reverse side of the beaker such that the message can be seen through the beaker.

Thereafter, the hotplate of a heatable laboratory stirrer unit (MR-Hei-Standard) is set to 200° C. and the speed to 600 rpm. On attainment of an internal temperature of the liquid of 140° C., the target temperature was once again raised to 250° C. The dissolution temperature has been attained when the message is just clearly readable through the liquid.

Result: (rounded mean from two measurements)
Example 1 (furanoate): 159° C.
Example 2 (phthalate): 161° C.
Example 3 (terephthalate): greater than 185° C. (stopped)

The dissolution temperature of the terephthalate could not be determined since PVC decomposition is to be expected above 185° C., and so the test was stopped.

The inventive furanoate exhibits the lowest dissolution temperature. This means that the inventive furanoate has a lower processing temperature than the plasticizers of Examples 2 and 3.

Example 5

Production of the Dry Blend, Measurement of Plasticizer Absorption and of Torque The advantageous properties achievable with the inventive esters are to be demonstrated hereinafter by way of example using dry blends, and the semifinished products obtainable therefrom.

The formulations produced, comprising the plasticizers of Examples 1 to 3, are shown in Table 1 below. These can be used to produce cable and wire insulations in particular.

TABLE 1

Formulations of the dry blends (All figures in parts by mass)

| Dry blend | 1* | 2** | 3** |
|---|---|---|---|
| Solvin S 271 PC | 100 | 100 | 100 |
| diisotridecyl furandicarboxylate | 50 | | |
| diisotridecyl phthalate | | 50 | |
| diisotridecyl terephthalate | | | 50 |
| OMYA BSH | 20 | 20 | 20 |
| Baeropan MC 8890 KA/2 | 8 | 8 | 8 |

**= comparative example
*= inventive

The materials and substances used are illustrated in detail below:
Solvin S 271 PC: suspension PVC with a K value (determined to DIN EN ISO 1628-2) of 71; from SOLVIN S.A.
OMYA BSH: mineral filler based on calcium carbonate, from OMYA
Baeropan MC 8890 KA/2: thermal stabilizer based on Ca/Zn for high-temperature applications, from Baerlocher The dry blend was produced in a Brabender planetary mixer. A thermostat filled with demineralized water (from Lauda RC6) ensured the temperature control of the mixing vessel on the planetary mixer. A PC recorded the data transmitted by the mixer via a data cable in the "Winmix" software.

The "Winmix" software was used to set the following parameters on the Brabender planetary mixer.

Speed programme: active
Profile: speed: 50 rpm; hold time: 9 min; rise time: 1 min speed: 100 rpm; hold time: 20 min
Kneader temperature: 88° C.
Measurement range: 2 Nm
Damping: 3

A temperature of 90° C. was set on the thermostat, and a hose connection was used for temperature control of the mixing vessel on the Brabender. The temperature in the mixing vessel was 88° C. after one hour of heating time. After the planetary mixer had conducted an internal calibration, the solid constituents (PVC, filler, stabilizer), which had been weighed beforehand into a PE cup in four times the amount on a balance (from Mettler, model XS6002S), were supplied to the mixing vessel via a solids funnel and the introduction stub present on the Brabender mixing vessel. The programme was started and the powder mixture was stirred and heated for 10 minutes in the mixing vessel until the liquid constituents, which had likewise been weighed into a PE cup in four times the amount on the balance, were supplied via a liquids funnel and the introduction stub present on the Brabender mixing vessel. The mixture was stirred for a further 20 minutes in the planetary mixer. After the programme had ended, the finished dry blend (powder) was removed. The transmitted torque-time diagram was evaluated using the BRABENDER software. After the addition of the liquid constituents, a distinct rise in the curve is evident. Only when the curve clearly declines again is the plasticizer absorption complete. The time difference between these two points is the plasticizer absorption time (called dry blend time). The maximum torque is automatically evaluated by the programme. The plasticizer absorption and the maximum torque determined in the production of the dry blends are shown in Table 2.

TABLE 2

Time required for the absorption of the liquid formulation components by the preheated PVC (plasticizer absorption) and the maximum torque determined in the course of production of the dry blends.

| Dry blend | A* | B** | C** |
|---|---|---|---|
| Plasticizer absorption [min.] | 9.2 | 11.1 | Not determinable, material remains moist |
| Maximum torque [Nm] | 1.7 | 1.5 | Not determinable |

**= comparative example
*= inventive

By virtue of the shorter mixing time associated with the shorter time for the plasticizer absorption, the processing speed of the inventive mixture is much higher than that of the comparative formulation from the prior art. The terephthalate does not appear to be sufficiently to adsorbed by the PVC under the test conditions. The use of the inventive plasticizer enables provision of dry blends which allow a higher processing speed compared to the prior art.

Example 6

Production of Milled Sheets and Pressed Slabs from Dry Blends

The dry blends described in Example 5 were used to produce milled sheets. The milled sheets were produced on a W150 AP calender from Collin. The Collin calender has an automatic sample reverser and the temperature is controlled by means of an additional oil thermostat (from Single, model: STO 1-6-12-DM). The control is effected by means of software from Collin.

The following parameters were set on the calender:
Roll temperature [° C.]: 170
Roll time [min]: 5 min
Five-stage programme for production of the milled sheet:
1$^{st}$ stage: plasticization of the dry blend
2$^{nd}$ stage: roll nip adjustment
3$^{rd}$ stage: melt mixing
4$^{th}$ stage: milled sheet optimization
5$^{th}$ stage: milled sheet removal After the attainment of the roll temperature, the roll nip was calibrated. To start the measurement, the roll nip was set to 0.2 mm. In each case 160 grams of a dry blend from Example 5 were weighed in and introduced into the roll nip with the rollers stationary. The programme was started. The rolls started with a rotation rate of 5 rpm and a friction of 20%. After approx. 1 min, the plasticization was for the most part complete and the roll nip was increased to 0.5 mm. This was followed by homogenization 6 times by means of an automatic reversal unit on the calender. After 5 min, the milled sheet was removed from the roller and cooled.

The terephthalate-containing dry blend (ester according to Example 3, dry blend C from Example 5) could not be used to produce a milled sheet either under the conditions specified or at a temperature increased by 10° C., since no plasticization was achievable on the roller. Therefore, the terephthalate-containing dry blend (Example C) was not included in the further studies.

Production of the Pressed Slabs

The pressed slabs were produced on a laboratory press from Collin. The prefabricated milled sheets (see above) were used for production of the pressed slabs. The margins of the milled sheets were removed with the aid of a cutting machine; the milled sheet was then cut into pieces of approx. 14.5×14.5 cm in size. For pressed slabs of thickness 1 mm, 2 pieces of milled sheet were each placed into the stainless steel pressing frame of 15×15 cm in size.

The following parameters were set on the laboratory press:
Three-phase programme:
Phase 1: both plates 175° C.; press platen pressure: 5 bar; phase time: 60 seconds.
Phase 2: both plates 175° C.; press platen pressure: 200 bar; phase time: 120 seconds.
Phase 3: both plates 40° C.; press platen pressure: 200 bar; phase time: 270 seconds.
The excess pressing lip was removed after production of the pressed slabs.

Example 7

Determination of the Plasticizing Action or Plasticizer Efficiency on Pressed Slabs by Determining the Shore Hardness (Shore D)

The Shore hardness is a measure of the softness of a test specimen. The further a standardized needle can penetrate into the test specimen in a particular test duration, the lower the measurement is. The plasticizer with the greatest efficiency gives the lowest Shore hardness value with the same amount of plasticizer. Since formulations are frequently adjusted or optimized for a particular Shore hardness in practice, it is accordingly possible to dispense with a particular proportion in the formulation in the case of very efficient plasticizers, which means a reduction in costs for the processor.

The hardness measurements were conducted at 25° C. to DIN 53 505 with a Shore D measuring instrument from Zwick-Roell (6 plane-parallel slabs of thickness 1 mm placed one on top of another); the measurement in each case was read off after 3 seconds. On each test specimen (produced according to Example 6), measurements were conducted at three different points, and an average was formed.

It should be noted here that the Shore hardness was not measured until 24 hours after production of the test specimens (storage at 25° C.). The results of the hardness determination are compiled in Table 3.

TABLE 3

Shore D hardness on pressed slabs produced according to Example 6

| | Test specimen formed from dry blend according to Ex. | | |
|---|---|---|---|
| | A* | B** | C** |
| Shore D | 42 | 44 | n.d. |

**= comparative example
*= inventive

Thus, plasticized polymers are provided, which have an improved efficiency compared to the phthalate plasticizers used as the comparative product and therefore lead especially to lower formulation costs.

Example 8

Volatility of the Plasticizer from Test Specimens

The test specimens from Example 6 were stored at 120° C. in a forced air heating cabinet (from Memmert) for 7 days. Before each weighing, the samples were equilibrated at room temperature in a desiccator for one hour.
Result (average from 6 samples in each case):
Loss of mass from Example 1 (furandicarboxylate): 0.72%
Loss of mass from Example 2 (phthalate): 0.85%

The inventive products have a lower volatility compared to the corresponding comparative example C13-phthalate. Thus, corresponding flexible PVC products would have a longer lifetime.

The invention claimed is:

1. A $C_{11}$ to $C_{13}$ dialkyl ester of furandicarboxylic acid.

2. A plasticizer or plasticizer composition, comprising at least one $C_{11}$ to $C_{13}$ dialkyl ester of claim 1.

3. The plasticizer or plasticizer composition of claim 2, wherein the $C_{11}$ to $C_{13}$ dialkyl ester is at least one $C_{11}$ to $C_{13}$ dialkyl furan-2,5-dicarboxylate.

4. The plasticizer or plasticizer composition of claim 2, wherein the $C_{11}$ to $C_{13}$ dialkyl ester is a mixture of at least two isomeric $C_{11}$ to $C_{13}$ dialkyl furan-2,5-dicarboxylates.

5. The plasticizer or plasticizer composition of claim 4, wherein the at least two isomeric $C_{11}$ to $C_{13}$ dialkyl furan-2,5-dicarboxylates comprise isomeric $C_{11}$ to $C_{13}$ alkyl groups.

6. The plasticizer or plasticizer composition of claim 4, wherein none of the at least two isomeric $C_{11}$ to $C_{13}$ dialkyl furan-2,5-dicarboxylates has a proportion of more than 90% by weight in the ester mixture.

7. The plasticizer or plasticizer composition of claim 5, wherein the isomeric $C_{11}$ to $C_{13}$ alkyl groups are at least one selected from the group consisting of an unbranched alkyl group, a singly branched alkyl group, a doubly branched alkyl group, a triply branched alkyl group, and a quadruply branched alkyl group.

8. The plasticizer or plasticizer composition of claim 2, wherein the $C_{11}$ to $C_{13}$ dialkyl ester is ditridecyl furan-2,5-dicarboxylate.

9. The plasticizer or plasticizer composition of claim 2, further comprising at least one additional compound selected from the group consisting of an alkyl benzoate, a dialkyl adipate, a glyceryl ester, a trialkyl citrate, an acylated trialkyl citrate, a trialkyl mellitate, a glycol dibenzoate, a dialkyl terephthalate, a dialkyl phthalate, a dialkanoyl ester of isosorbitol, and a dialkyl ester of 1,2-, 1,3- or 1,4-cyclohexanedicarboxylic acid.

10. A process for preparing the plasticizer or plasticizer composition of claim 2, the process comprising:
   a) reacting a stoichiometric excess of one or more $C_{11}$-$C_{13}$-alcohols, in the presence of a metal catalyst, with a furandicarboxylic acid or a derivative of the furandicarboxylic acid;
   b) removing excess alcohol after complete conversion of the furandicarboxylic acid or of the derivative of the furandicarboxylic acid, to obtain a reaction mixture; and
   c) working up the reaction mixture to obtain the plasticizer or plasticizer composition.

11. An adhesive, a sealing compound, a coating composition, a lacquer, a paint, a plastisol, a paste, a synthetic leather, a floor covering, an underbody protection, a fabric coating, a wallpaper, a cable, a wire insulation, a film, an automobile interior application or an ink, comprising the plasticizer or plasticizer composition of claim 2.

12. A polymer composition, comprising a polymer and the plasticizer of claim 2.

13. The polymer composition of claim 12, wherein the polymer is at least one selected from the group consisting of a polyvinyl chloride (PVC), a polyvinylidene chloride (PVDC), a polyacrylate, a polymethyl methacrylate (PMMA), a polyalkyl methacrylate (PAMA), a fluoropolymer, a polyvinylidene fluoride (PVDF), a polytetrafluoroethylene (PTFE), a polyvinyl acetate (PVAc), a polyvinyl alcohol (PVA), a polyvinyl acetal, a polyvinyl butyral (PVB), a polystyrene polymer, a polystyrene (PS), an expandable polystyrene (EPS), an acrylonitrile-styrene-acrylate (ASA), a styrene acrylonitrile (SAN), an acrylonitrile-butadiene-styrene (ABS), a styrene-maleic anhydride copolymer (SMA), a styrene-methacrylic acid copolymer, a polyolefin, a polyethylene (PE), a polypropylene (PP), a thermoplastic polyolefin (TPO), a polyethylene-vinyl acetate (EVA), a polycarbonate, a polyethylene terephthalate (PET), a polybutylene terephthalate (PBT), a polyoxymethylene (POM), a polyamide (PA), a polyethylene glycol (PEG), a polyurethane (PU), a thermoplastic polyurethane (TPU), a polysulphide (PSu), a biopolymer, a polylactic acid (PLA), a polyhydroxybutyral (PHB), a polyhydroxyvaleric acid (PHV), a polyester, a starch, a cellulose, a cellulose derivative, a nitrocellulose (NC), an ethylcellulose (EC), a cellulose acetate (CA), a cellulose acetate/butyrate (CAB), a rubber and a silicone.

14. The polymer composition of claim 12, comprising the plasticizer in an amount of 5 to 200 parts by mass per 100 parts by mass of the polymer.

15. The polymer composition of claim 12, wherein a mass ratio of the plasticizer to the polymer is in a range from 1:15 to 15:1.

16. The polymer composition of claim 12, wherein the polymer is a copolymer of vinyl chloride with one or more monomers selected from the group consisting of vinylidene chloride, vinyl acetate, vinyl propionate, vinyl butyrate, vinyl benzoate, methyl acrylate, ethyl acrylate and butyl acrylate.

17. A moulding or film, comprising the polymer composition of claim 12.

18. The moulding or film of claim 17, wherein the film or moulding is a floor covering, a wall covering, a hose, a profile, a roofing sheet, a sealing sheet, a cable or wire sheath, a tarpaulin, an advertising banner, synthetic leather, packaging film, a medical article, a toy, a seal, an automobile interior article or a furnishing article.

19. The plasticizer or plasticizer composition of claim 5, wherein none of the isomeric $C_{11}$ to $C_{13}$ dialkyl furan-2,5-dicarboxylates has a proportion of more than 90% by weight in the ester mixture.

20. The plasticizer or plasticizer composition of claim 7, wherein none of the isomeric $C_{11}$ to $C_{13}$ dialkyl furan-2,5-dicarboxylates has a proportion of more than 90% by weight in the ester mixture.

21. The process of claim 10, wherein the metal catalyst comprises at least one metal selected from the group consisting of tin, titanium and zirconium.

22. The process of claim 10, wherein the metal catalyst is at least one selected from the group consisting of a tin powder, a tin (II) oxide, a tin (II) oxalate, a titanium ester, and a zirconium ester.

23. The process of claim 10, wherein the metal catalyst is at least one selected from the group consisting of tetraisopropyl orthotitanate, tetrabutyl orthotitanate and tetrabutyl zirconate.

* * * * *